United States Patent [19]
Hattori et al.

[11] Patent Number: 5,209,882
[45] Date of Patent: May 11, 1993

[54] MEANS AND METHOD FOR FORMING SYRINGE

[75] Inventors: Takeshi Hattori, Tokyo; Kuniyuki Onzuka, Oita; Yoshiyuki Ichizawa, Saitama, all of Japan

[73] Assignees: Sunstar Kabushiki Kaisha, Osaka; Yoshino Kogyosho Co., Ltd., Tokyo, both of Japan

[21] Appl. No.: 710,000

[22] Filed: Jun. 4, 1991

[51] Int. Cl.$^5$ .................. B29C 53/08; B29C 55/24
[52] U.S. Cl. .................. 264/40.2; 264/138; 264/164; 264/291; 264/295; 264/296; 264/339; 425/169; 425/304; 425/306; 425/324.1; 425/394; 425/397; 425/402
[58] Field of Search ........... 425/215, 296, 297, 302.1, 425/304, 306, 324.1, 394, 397, 402, DIG. 53, 169, 173; 264/138, 164, 291, 339, 295, 296, 40.2; 604/187, 218; 422/100; 65/108, 109, 158, 276, 278, 279, 281, 283, 292

[56] References Cited

U.S. PATENT DOCUMENTS

| | | | |
|---|---|---|---|
| 2,272,105 | 2/1942 | Anastor | 65/281 |
| 2,571,416 | 10/1951 | Brown | 264/339 |
| 2,698,501 | 1/1955 | Peek, Jr. et al. | 65/281 |
| 3,608,146 | 9/1971 | Dunipace | 425/DIG. 53 |
| 3,719,737 | 3/1973 | Vaillancourt et al. | 264/296 |
| 3,736,099 | 5/1973 | Begg et al. | 422/100 |
| 4,212,204 | 7/1980 | St. Armand | 264/232 |
| 4,834,637 | 5/1989 | Conta et al. | 425/173 |
| 4,904,437 | 2/1990 | Muhlbauer | 264/295 |
| 4,963,306 | 10/1990 | Weldon | 264/295 |
| 5,032,343 | 7/1991 | Jeffs et al. | 425/577 |

FOREIGN PATENT DOCUMENTS

| | | | |
|---|---|---|---|
| 0182943 | 6/1986 | European Pat. Off. | 422/100 |
| 1479951 | 9/1969 | Fed. Rep. of Germany | 425/302.1 |
| 53-21234 | 7/1978 | Japan. | |
| 3-105238 | 5/1991 | Japan | 425/169 |

*Primary Examiner*—Jay H. Woo
*Assistant Examiner*—Robert B. Davis
*Attorney, Agent, or Firm*—Oliff & Berridge

[57] ABSTRACT

In a first forming stage, the bottom portion of a monomolded plastic syringe (a type wherein the whole portion, i.e., a main syringe body and a needle portion, is molded unitedly in a cast) is heated and then stretched to a certain length, forming the edge portion like a needle, while the syringe is intermittently moved. Then the sryinge is carried to a second forming stage, where the syringe is moved intermittently and the needle portion is heated, then it is bent at a certain angle and is cut in a certain length, forming a completed syringe.

4 Claims, 5 Drawing Sheets

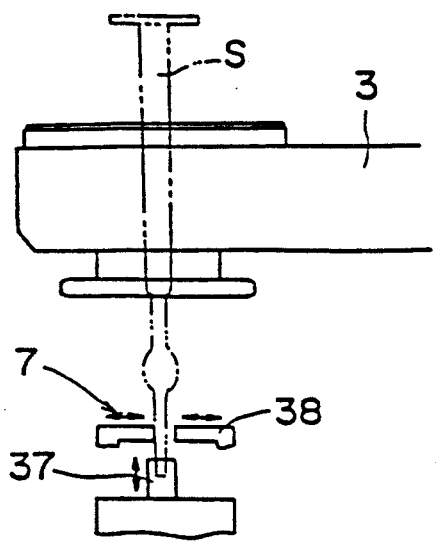
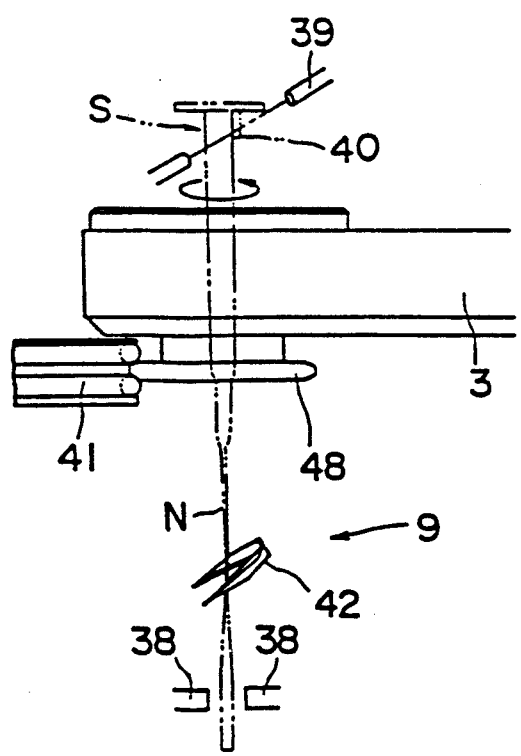

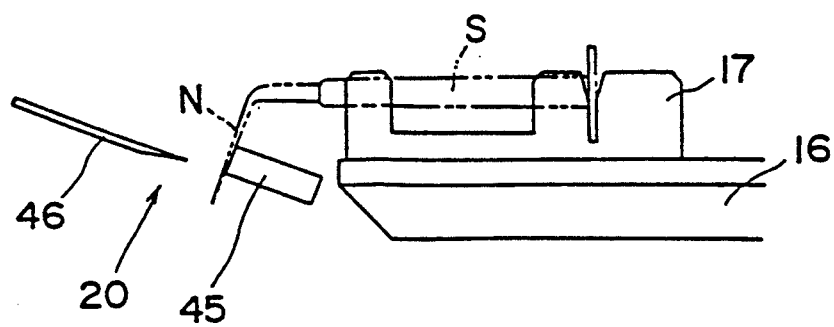
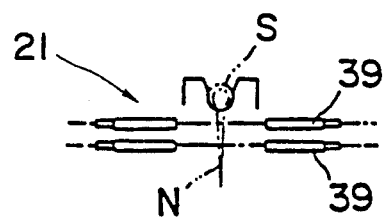
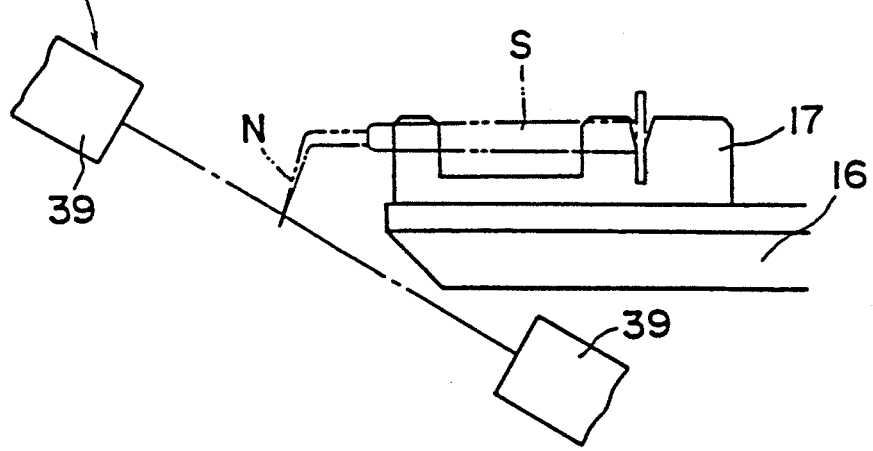

MEANS AND METHOD FOR FORMING SYRINGE

BACKGROUND OF THE INVENTION

The present invention relates to a means and method of forming a needle portion of a plastice syringe, which is used, for example, for dental surgery.

Among syringes used for dental surgery, there is a type that the edge portion thereof is bent at a certain angle. This type of syringe comprises a glass made syringe tube and a steel made needle secured to the edge of the tube. This type of syringe is repeatedly used after washing, which is undesirable when a sanitary condition is concerned. Therefore, inexpensive and disposable plasitic syringes have been used recently.

Such a plastic syringe is shown, for example, in Japanese patent publication 53-21234. This syringe comprises a plastic syringe tube and a plastic thin tube which is formed separately from the syringe tube and is secured to the edge of the syringe tube, then the thin tube is heated and sharpened like a needle.

The problem with this prior art is that since the syringe tube and the thin tube are formed separately and are combined together thereafter, a lot of time is required for completing a syringe, so that productivity thereof is not satisfactory. Further, when the thin tube is heated and sharpened, some handwork has to be applied, so that a lot of experience and time are required, which detracts from productivity. Since the handwork is required, the shape of the syringe is not always accurate.

This type of syringe is supposed to be disposable, so that it should be produced by mass production and the price thereof should be kept low. However, the prior art syringe explained above is expensive, since its productivity is poor.

OBJECTS OF THE INVENTION

The object of the present invention therefore is to provide a means and method which mass produces plastic syringes, of a type where needles thereof are bent at a certain angle, with high accuracy.

BRIEF DESCRIPTION OF THE INVENTION

FIG. 4 is a side elevational view of a lifter, lifting a syringe upward.

FIG. 5 is a side elevational view of a phototube and a second revolver accurately positioning a syringe, and a first cutter, cutting a needle portion of the syringe.

FIG. 9 is a side elevational view of a second cutter, cutting a syringe.

FIG. 10 is an elevational view of phototubes, checking a bent angle of a syringe.

FIG. 11 is a side elevational view of a phototube, reading a outside diameter of a needle of a syringe.

DESCRIPTION OF THE INVENTION

Figure 1:
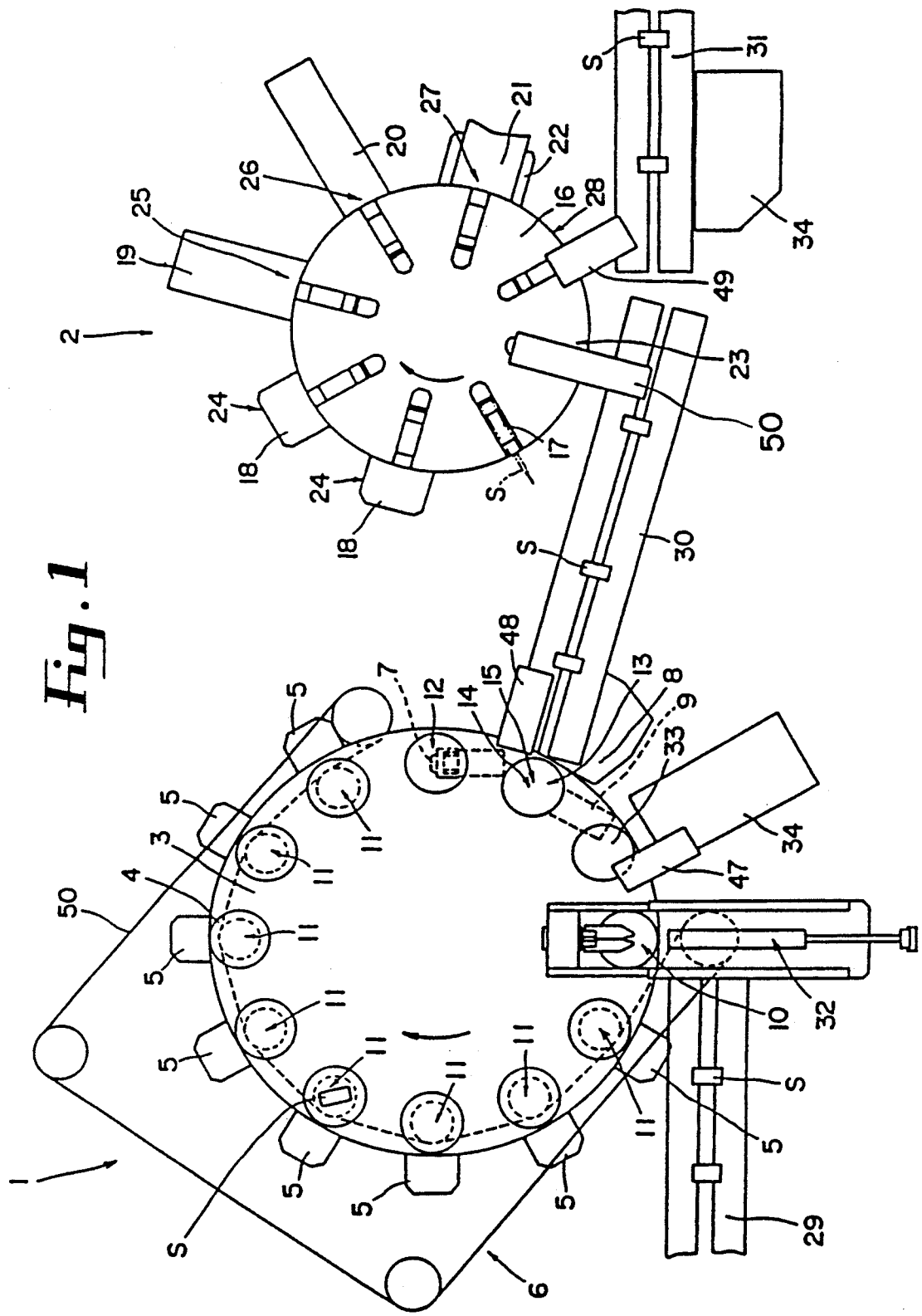
FIG. 1 is a brief top view of the preferred embodiment of the present invention.

A means according to the present invention comprises a first forming means 1 and a second forming means 2.

The first forming means 1 at least heats the edge portion of a mono-molded plastic syringe (s) (which is of a type that a whole portion including a main body of a syringe and a needle portion thereof is molded unitedly in the same cast), and stretches it to a certain length, forming a needle (n). The second forming means 2 at least re-heats the needle (n) of the syringe which is carried from the first forming means 1, and bends the needle (n) at a certain angle and cuts it in a certain length.

The first forming means 1 can be arranged to comprise a first table 3, first holder 4, first heater 5, first revolver 6, stretcher 7, positioner 8 and first cutter 9.

The first table 3 is shaped like a diso and revolves intermittently carrying syringes to a first carry-in section 10, first heating section 11, stretching section 12, positioning section 13, first cutting section 14 and first carry-out section 15, which are positioned in order. The first holders 4 are positioned around the edge portion of the first table 3 at regular intervals, and each of them holds a syringe in a standing position. The first heater 5 is secured to the first heating section 11 to heat the bottom edge portion of a syringe (s). The first revolver 6 revolves the first holder 4 positioned in the first heating section 11. The stretcher 7 is placed in the stretching section 12 and stretches the bottom edge portion of a syringe (s) to form a needle (n). The positioner 8 is placed in the positioning section 13 and positions a sryinge (s) in a certain direction. The first cutter 9 is positioned in the first cutting section 14 and cuts a needle (n) of a syringe (s), which has been stretched to a certain length.

The second forming means 2 can be arranged to comprise a second table 16, second holder 17, second heater 18, bender 19, second cutter 20, angle reader 21 and outside diameter reader 22.

The second table 16 is also shaped like a disc and revolves intermittenly conveying a syringe (s) to a second carry-in section 23, second heating section 24, bending section 25, second cutting section 26, reading section 27 and second carry-out section 28. The second holders 17 are positioned around the edge portion of the second table 16 at regular intervals and each holds a syringe (s) in a lying position with its needle (n) facing in an outward direction.

The second heater 18 is placed in the second heating section 24 and re-heats a needle (n) of a syringe (s). The bender 19 is positioned in the bending section 25 and bends a needle (n) at a certain angle. The second cutter 20 is located in the second cutting section 26 and cuts a bent needle (n) in a certain length. The angle reader 21 is placed in the reading section 27 and reads an angle of a needle (n). The outside diameter reader 22 is placed in the reading section 27 and measures an outside diameter of a needle (n).

Figure 2:
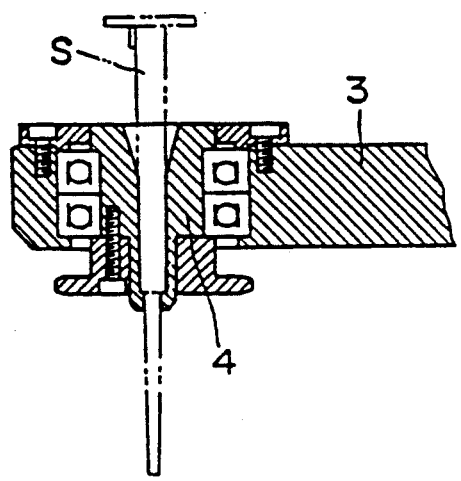
FIG. 2 is a sectional view showing a combination of a syringe and a first holder of the preferred embodiment of the present invention.
Figure 3:
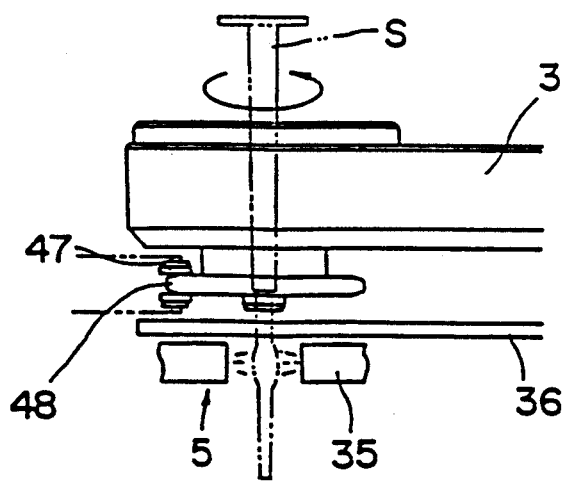
FIG. 3 is a side elevational view of a first heater, heating a syringe.

The function of the present invention will be described below. First, a plastic syringe (s), which has been conveyed to the first carry-in section 10 of the first forming means 1, is held by the first holder 4 in a standing position (see FIG. 2). Then, the first table 3 revovles intermittently and conveys the syringe (s) to the first heating section 11, where the bottom portion of the syringe (s) is heated by the first heater 5. The first holder 4 positioned in the first heating section 11 is revolved by the first revolver 6, so that the syringe (s) revolves with it and the bottom portion of the syringe (s) can be heated evenly (FIG. 3). After the heating poroces in the first heating section 11 is completed, the heated syringe (s) reaches the stretcher 12, where the bottom portion thereof is stretched to a certain length by the stretcher 7. By this stretching process, a needle (n) is formed at the bottom of the syringe (s). Since the bottom portion of the syringe (s) is heated before stretching, the heated portion is well stretched when pulled by the stretcher 7 (FIG. 4 and 5). The syringe (s) comprising the needle (n) at its bottom portion, then arrives at the positioning section 13, where the syringe (s) is positioned to a certain direction and the needle (n) is cut in a certain length (FIG. 5). Thereafter, the syringe (5) is conveyed to the first carry-out section 15 and then it is carried away.

Figure 6:
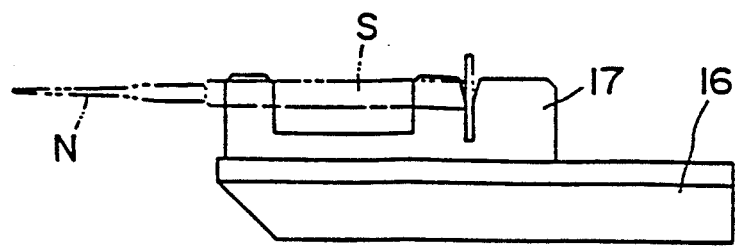
FIG. 6 is a side elevational view showing a combination of a syringe and a second holder.
Figure 7:
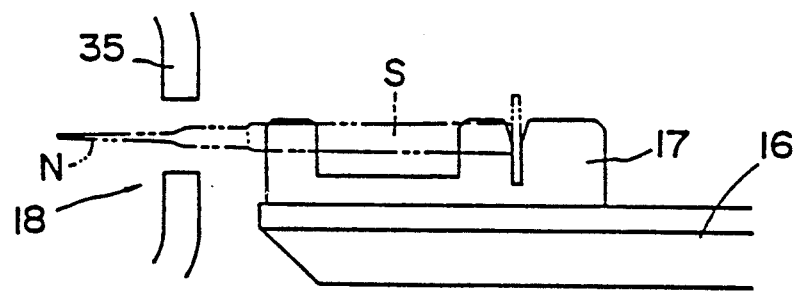
FIG. 7 is a side elevational view of a second heater, heating a syringe.
Figure 8:
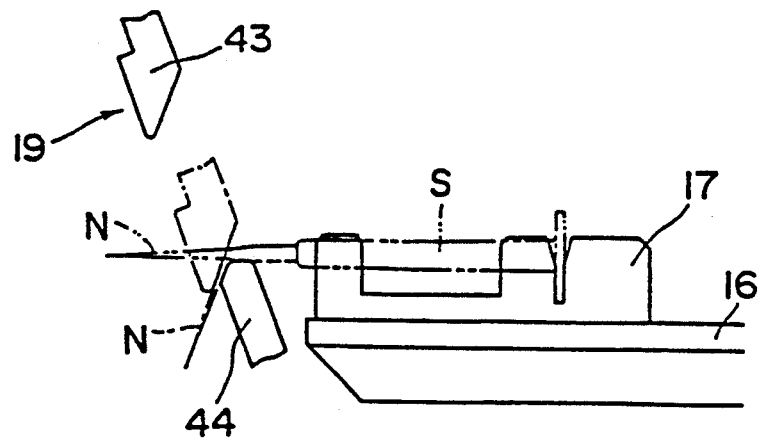
FIG. 8 is a side elevational view of a bender, bending a syringe.

The plastic syringe (s) carried out from the first forming means 1 is then conveyed by a second conveyer 30 to the second forming means 2, where the syringe (s) is conveyed to the second carry-in section 23 and it is held by the second holder 17 in a lying position with its needle (n) facing in an outward direction (FIG. 6). Then, the second table 16 revolves intermittently conveying the syringe (s) to the second heating section 24, where the needle (n) is heated by the second heater 18 (FIG. 7). The syringe (s) is then conveyed to the bending section 25, where the needle (n) is bent at a certain angle by the bender 19. Since the certain portion is heated in advance, the bending process is completed smoothly (FIG. 8). The needle (n) being bent at a certain angle is then cut in a certain length by the second cutter 20 of the second cutting section 26 (FIG. 9). It is possible to locate the bending section 25 and the second cutting section 26 in the same place and accomplish the bending and cutting processes of the needle (n) at the same time. After finishing the bending and cutting processes of the needle (n), the syringe (s) is conveyed to the reading section 27, where the angle of the needle (n) is read by the angle reader 21 (FIG. 10) and also the outside diameter of the needle (n) is measured by the outside diameter reader 22 (FIG. 11). Then, the syringe 27 is conveyed to the second carry-out section 28 and is carried away.

PREFERRED EMBODIMENT OF THE INVENTION

FIGS. 1 to 11 show a preferred embodiment of the present invention.

A first conveyer 29 is connected to the first carry-in section 10 of the first forming means 1, and a plastic syringe (s) is conveyed by the first conveyer 29 in an upright standing position. The syringe (s) is then carried into the first table 3 by a first carry-in means 32 secured near the first carry-in section 10, and the syringe (s) is held by the first holder 4 in the same standing position (see FIG. 2). This syringe (s) is made of plastic, and a whole portion such as a syringe body portion and a needle portion are formed unitely by an injection mold.

In the preferred embodiment of the present invention, the first forming means 1 comprises eight first heating sections 11 in the first table 3 at regular intervals, each of them comprising a first heater 5. The first holder 4 positioned in the first heating section 11 is revolved by the first revolver 6 which transmits its power to a sprocket 48 via a chain. As the syringe (s) held by the first holder 4 revolves, the bottom portion of the syringe (s) is heated evenly. Each first heater 5 applies hot air through a nozzle 35, which heats the bottom portion of the syringe (s). A cover plate 36 is installed to prevent the hot air from affecting its heat waves to the rest portion of the syringe (s) (FIG. 3).

The stretcher 7 moves downward while a clamp 38 thereof holding underneath of the heating portion of the syringe (s), so that the heating portion is stretched (FIG. 4). The distance of the downward movement of the stretcher 7 is fixed, so that the shape such as an outlook, inside diameter and outside diameter of the needle (n) is evenly regulated.

In the preferred embodiment of the present invention, the lifter 37 lifts the bottom edge of the syringe (s) to a certain range before stretching the bottom portion of the syringe (s) (FIG. 4). When the bottom portion of the syringe (s) is heated, the heated portion melts and the bottom portion of the syringe (s) elongates by its own weight and by an expansion effect, so that the length of the bottom portion prior to the stretching process becomes uneven. When a length of a syringe (s) is shorter or longer than the desired length, the final length thereof becomes shorter or longer, which causes the formation of an irregularized shape of needle (n).

In the preferred embodiment, the syringe (s) having a stretched needle (n) is positioned to a certain direction by the phototube 39. This positioning is completed such that the syringe (s) is revolved by the second revolver 41, and when the a light beam of the phototube 39 is cut by a projection 40 situated to the upper portion of the syringe (s), the revolution of the syringe (s) stops (FIG. 5). The positioning of the syringe (s) is required to adjust a scale written on the syringe (s) and an angle of the needle (n) in a certain direction.

After the positioning of the syringe (s) is done, the needle (n) is cut, in the same section, in a certain length by scissors 42 (FIG. 5).

After completing the cutting process of the needle (n), the syringe (s), keeping its standing position, is conveyed to the second conveyer 30 by the first carry-out means 48, and is carried to the second forming means 2 by the second conveyer 30. Inferior products are intermittently moved to the poor goods carry-out section 33 and are carried out in the disposal container 34 by the poor goods carry-out means 47.

The syringe (s), conveyed by the second conveyer 30, is lied down and carried to the second carry-in section 23 of the second forming means 2 by the second carry-in means 50, and it is held by the second holder 17 (FIG. 6). The processes of lying down the syringe (s) from its standing position and conveying the syringe (s) from the second conveyer 30 to the second holder 17 is achieved by the second carry-in means 50.

The second forming means 2 comprises two second heating sections 24 consecutively, and each of them comprises a second heater 18. The second heater 18 also provides hot air from its nozzle 35 and re-heats the needle (n) of the syringe (s) (FIG. 7). The re-heated needle (n) of the syringe (s) is bent at a certain angle by cooperation of the press block 43 and the support block 44 (FIG. 8). After completing the bending process, the needle (n) of the syringe (s) is cut in a certain length by cooperation of the upper edge 45 and the lower edge 46 (FIG. 9). In this preferred embodiment, although the bending section 25 and the second cutting section 26 are positioned at a different area, they can be positioned in the same section to accomplish the cutting process right after the bending process is done.

The angle reader 21 which reads an angle of the needle (n) is arranged such that it emits a plural number of light beams to a number of certain parts of the needle (n) of the syringe (s) (FIG. 10). The outside diameter reader 22 which measures an outside diameter of the needle (n) is composed of the phototube 39 which emits a light beam to the needle (FIG. 11).

After the angle and the outside diameter are read, qualified syringes (s) are moved back to the standing position from the lying position, and are conveyed to the third conveyer 31 by the second carry-out means 49, and are carried away by the third conveyer 31. Inferior syringes (s) are put in a disposal container 34.

As described, according to the present invention, the needles (n) of the unitedly made plastic syringes (s) can be automatically mass formed with high accuracy, so that disposable syringes (s) can be provided with an inexpensive price, and which contribute to better sanitary conditions in many fields such as dental surgery.

What we claim is:

1. A means for forming a syringe, comprising:
   a first forming means being arranged to heat the bottom portion of a mono-molded plastic syringe, stretch said bottom portion to a certain length, form a needle and cut it in a certain length;
   and a second forming means being arranged to heat said needle of said syringe conveyed from said first forming means, bend said needle at a certain angle and cut it in a certain length.

2. The means for forming a syringe as claimed in claim 1, wherein said first forming means, further comprises:
   a first table, said first table being shaped like a disk and arranged to revolve intermittently conveying said syringe to a first carry-in section, a first heating section, a stretching section, a positioning section, a first cutting section and a first carry-out section, which are positioned in order;
   a plural number of first holders being positioned around the edge portion of said first table at regular intervals, holding said syringe in an upright standing position;
   a first heater being positioned in said first heating section and arranged to heat said needle of said syringe;
   a first revolver being arranged to revolve said first holders in said first heating section;
   a stretcher being positioned in said stretching section and arranged to stretch the bottom portion of said syringe to form said needle;
   a positioner being positioned in said positioning section and arranged to position said syringe in a certain direction;
   and a first cutter being positioned in said first cutting section and arranged to cut said needle in a certain length.

3. The means for forming a syringe as claimed in claim 1, wherein said second forming means, further comprises:
   a second table, said second table being shaped like a disk and arranged to revolve intermittently conveying said syringe to a second carry-in section, a second heating section, a bending section, a second cutting section, a reading section and a second carry-out section, which are positioned in order;
   a plural number of second holders being positioned around the edge portion of said second table at regular intervals and arranged to hold said syringe in a lying position with its needle facing in an outward direction;
   a second heater being positioned in said heating section and arranged to heat said needle;
   a bending means being positioned in said bending section and arranged to bend said needle at a certain angle;
   a second cutter being positioned in said second cutting section and arranged to cut said needle of said syringe in a certain length;
   an angle reader being positioned in said reading section and arranged to read an angle of said needle of said syringe;
   and an outside diameter reader being positioned in said reading section and arranged to measure an outside diameter of said needle of said syringe.

4. Method for forming a syringe, comprising the steps of:
   a first heating step, wherein a bottom portion of a syringe is heated and softened;
   a stretching step, wherein said bottom portion of said syringe is stretched a certain amount along a longitudinal axis of said syringe, said bottom portion being formed as a needle portion of said syringe and said needle portion being cut to a certain length;
   a second heating step, wherein the base portion of said needle portion is heated and softened;
   a bending step, wherein said softened needle portion is bent at a certain angle;
   a cutting step, wherein said bent needle portion is cut to a certain length;
   and a reading step, wherein an angle reader and an outside diameter reader are arranged to read an angle and an outside diameter of said needle portion of said syringe, respectively.

* * * * *